(12) United States Patent
Fox et al.

(10) Patent No.: US 7,806,952 B2
(45) Date of Patent: Oct. 5, 2010

(54) APPARATUS, SYSTEM, AND METHOD FOR ENHANCING AIR PURIFICATION EFFICIENCY

(75) Inventors: Andrew R. Fox, Oakdale, MN (US); Marvin E. Jones, Grant, MN (US); Larry J. Carson, Maplewood, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 32 days.

(21) Appl. No.: 12/184,623

(22) Filed: Aug. 1, 2008

(65) Prior Publication Data

US 2010/0024652 A1    Feb. 4, 2010

(51) Int. Cl.
*B03C 3/70* (2006.01)

(52) U.S. Cl. ............ 55/360; 95/57; 95/78; 96/15; 96/63; 96/88; 96/97; 313/292; 313/313; 361/225; 361/235

(58) Field of Classification Search ........... 55/360; 95/57, 78; 96/15, 63, 88, 95–97; 313/238, 313/292, 309, 313, 326, 351; 323/903; 361/225–235
See application file for complete search history.

(56) References Cited

U.S. PATENT DOCUMENTS

| | | | |
|---|---|---|---|
| 3,234,432 A | 2/1966 | Streib | |
| 3,608,280 A * | 9/1971 | Martin | 96/140 |
| 4,089,618 A | 5/1978 | Patel | |
| 4,151,577 A | 4/1979 | Yavnieli et al. | |
| 4,250,431 A | 2/1981 | Sugarman | |
| 5,332,425 A | 7/1994 | Huang | |
| 5,407,469 A * | 4/1995 | Sun | 96/62 |
| 5,529,613 A * | 6/1996 | Yavnieli | 96/63 |
| 5,630,866 A * | 5/1997 | Gregg | 96/67 |
| 5,702,507 A * | 12/1997 | Wang | 96/55 |
| 6,758,884 B2 | 7/2004 | Zhang et al. | |
| 7,279,021 B2 * | 10/2007 | Haberlein | 55/360 |
| 7,381,248 B2 * | 6/2008 | Kim et al. | 96/61 |
| 2004/0025695 A1 * | 2/2004 | Zhang et al. | 96/59 |
| 2006/0278074 A1 | 12/2006 | Tseng et al. | |
| 2007/0034082 A1 * | 2/2007 | Adair et al. | 96/63 |
| 2010/0024652 A1 * | 2/2010 | Fox et al. | 96/58 |

FOREIGN PATENT DOCUMENTS

| | | | | |
|---|---|---|---|---|
| JP | 4-281862 A | * 10/1992 | | 96/88 |
| JP | 11-290716 | 10/1999 | | |

OTHER PUBLICATIONS

PCT International Search Report PCT/ISA/210 dated Feb. 24, 2010.

* cited by examiner

*Primary Examiner*—Richard L Chiesa
(74) *Attorney, Agent, or Firm*—David B. Patchett

(57) ABSTRACT

Disclosed are apparatus, system, and method for enhancing air purification efficiency regarding a gaseous medium passing through an opening. Included is a high voltage source that creates an effective voltage field across the opening; and at least one charge bleeding element constructed and arranged to maintain an effective voltage field across the opening.

10 Claims, 4 Drawing Sheets

APPARATUS, SYSTEM, AND METHOD FOR ENHANCING AIR PURIFICATION EFFICIENCY

BACKGROUND

The present description is directed to purification and filtering systems and methods and, more particularly, to purification and filtering systems, apparatus, and methods that have enhanced efficiency in terms of removing suspended contaminants in a gaseous medium, such as air.

Several air and gas particle purification and filtering systems and methods are known for purifying and filtering air of contaminants, such as odors, gases, smoke, pollen, dust, etc. Room air purifiers utilize filter elements that may include electrostatically charged fibers, since the latter have relatively high efficiencies for capturing charged particles from air passing through the filters.

One commercially available type is a room air purifier. Some room air purifiers are portable and include a filtration system, a fan, and a device for charging air molecules and particles. The filtration system typically includes a filter element(s) positioned intermediate or between intake and exhaust passages. A fan unit typically draws ambient air into the air purifier and through the filter elements before expelling it from the exhaust; in other embodiments the fan may draw air into the intake and then force air through the filter before passing through the exhaust. Often, in room air purifiers of this kind an ionizer generates ions in the flowing air stream for charging molecules in the air. Generated ions may be of positive polarity, negative polarity or a combination of both negative and positive polarity. Included in such approaches are high voltage electrodes in the form of wires(s), point(s), or brush(es) and the like. For example, the high voltage may be in the order of about +/−4-20 kV when measured with a high voltage meter having a 1 G$\Omega$ input impedance and about +/−4-30 kV when measured with a high voltage meter having 10 G$\Omega$ input impedance. The ionized air molecules within and exiting the air purifier are understood to rapidly transfer their charge to airborne contaminants including particles, odors, gases and the like. Some of the air and gas contaminants charged by the ionized air molecules become, through agglomeration, too heavy to remain in air and, hence, settle or precipitate to ground. Other charged contaminants are attracted to room surfaces (e.g., walls, etc.) surrounding the air purifier, and still others are drawn back into the air purifier by the suction of the fan to be trapped by the filter elements within the room air purifier. In some room air purifiers, the filter elements may be electrostatically charged so as to be particularly receptive to attracting electrostatically charged contaminants and this thereby increases removal efficiency. An example of this latter type of air purifier is commercially available from 3M Corporation, St. Paul, Minn. under the trade name FAP04-RC Ultra-Slim Air Purifier.

It has been determined that particle removal efficiencies of known air purifiers vary over a period of time. It is believed that such variations are at least a function of variations in ionization of the air passing through the room air purifier. The ionized species tend to accumulate or build-up on the surrounding surfaces of the air purifier. As such, these voltage fields tend to collapse which tends to lessen the efficiency of the overall performance since the flow of electrons and ion current decrease.

Known approaches have been attempted to provide for more consistent ionization of the flowing air. Some have used a brush to generate ions coupled with a reference ground wire to the interior of the housing near the ionizer discharge, that is a wire that is not attached to earth ground, but rather provides the low voltage reference from the ionizer transformer against which the high-voltage circuit is stepped-up. The ground wire created an isolated point ground. It has been determined that the foregoing point ground arrangement yielded inconsistent ionization results, as measured by inconsistencies in generally expected measurements of a Clean Air Delivery Rate (CADR) for small particles, such as 1 micron or less as, for example, tobacco smoke and combustion by-products.

Another approach included adding several strips of conductive tape on and around PC boards in an outlet of the air purifier and connecting them to the reference ground from the ionizer power supply. This arrangement did not appear successful in providing tangible benefits to the CADR.

Still another approach included using an exposed conductive strip several inches long (e.g., 7.5 inches) upstream of the ionizer discharge and connected to the interior of the housing. The exposed ground strip yielded erratic results and when a filter was installed, the ionizer discharge had no line of sight to ground source. This approach also did not yield results that improved the consistency of ionization across the discharge.

Other grounding schemes in air purifiers include a high voltage discharge electrode upstream of an exhaust outlet and a capped metal pin which is located normal to the discharge with respect to the airflow. A plastic shroud blocks direct line of sight between the discharge and ground pins. This kind of air purifier tends to be less effective at removing submicron contaminants and additionally some of such contaminants accumulate on the shroud and such accumulation may provide a conductive pathway between the high-voltage electrode and ground, thereby potentially providing a partial short circuit as well as a decrease in performance over extended periods of time.

Accordingly, none of the heretofore known air purifiers are as efficient over a period of time as could otherwise be desired because of their transitory effectiveness. Accordingly, there is a need for air purifier and methods associated therewith that are particularly useful for prolonging the effectiveness of the gas or air purification system so as to make them as efficient as could otherwise be desired.

SUMMARY

The present description is directed to a method of maintaining an effective voltage field over a period of time across an opening having a gaseous medium passing therethrough, wherein an electrostatic charge builds-up on structure surrounding the opening. The method comprises: providing at least a high voltage source within and/or adjacent the opening to create an effective voltage field across the opening; and controlling accumulation of charges on structure surrounding the opening that affect the voltage field by bleeding the charges therefrom in a manner that generally maintains the effective voltage field across the opening.

The present description is directed to a system that comprises: a housing assembly defining an opening allowing air to pass therethrough; a motor driven fan associated with the housing assembly and operable for driving the air through the opening downstream of the opening; at least a high voltage source within and/or adjacent the opening to ionize and transfer charges to molecules in the air, and create an effective voltage field across the opening; at least one charge bleeding element adjacent the opening and associated with the housing assembly with the bleeding element at a lower voltage potential than the high voltage source; and an insulating material between the bleeding element and the high voltage source for controlling migration of charges to the bleeding element that accumulate on the housing assembly so as to generally maintain an effective voltage field over a period of time across the opening.

The present description is directed to an air purifier apparatus for removing contaminants from air. The apparatus comprises: a housing assembly defining an opening allowing air to pass therethrough; a motor driven fan associated with the housing assembly and operable for driving the air through the opening downstream of the opening; at least a high voltage source within and/or adjacent the opening to ionize and transfer charges to molecules in the air, and create an effective voltage field across the opening; at least one charge bleeding element adjacent the opening and associated with the housing assembly with the bleeding element at a lower voltage potential than the high voltage source, and an insulating material between the bleeding element and the high voltage source for controlling migration of charges that accumulate on the housing assembly to the bleeding element so as to generally maintain an effective voltage field over a period of time across the opening; and a filter mechanism in the housing assembly and located upstream of the opening for removing contaminated particles from the air.

An aspect of the present description includes a method, system, and apparatus for providing a more consistent ionization of a gaseous medium, such as room air.

Another aspect of the present description includes a method, system, and apparatus, as noted above, for effectively controlling static discharge so as to maintain an effective predefined voltage field over a period of time across an opening through which the gaseous medium passes.

Another aspect of the present description includes a method, system, and apparatus, as noted above, for creating a voltage field over a period of time across the opening by a high voltage source that includes at least a point ionizer and an insulated bleeding electrode immediately adjacent the point ionizer from at least slightly upstream of the point ionizer to downstream of the point ionizer.

Another aspect of the present description includes a method, system, and apparatus, as noted above for controlling charges migrating through the insulation material to the bleeding electrode so as to prolong or maintain the effective voltage field over a period of time across the opening.

Another aspect of the present description is to accomplish the above in a manner that minimizes a likelihood that a fan motor will build-up or accumulate an excessive amount of electrostatic charge thereon.

Another aspect of the present description is to accomplish the above in a manner that is cost effective to manufacture, assemble, and use.

The aspects described herein are merely a few of the several that can be achieved by using the present description. The foregoing descriptions thereof do not suggest that the present description must only be utilized in a specific manner to attain the foregoing aspects.

DETAILED DESCRIPTION

Figure 1:
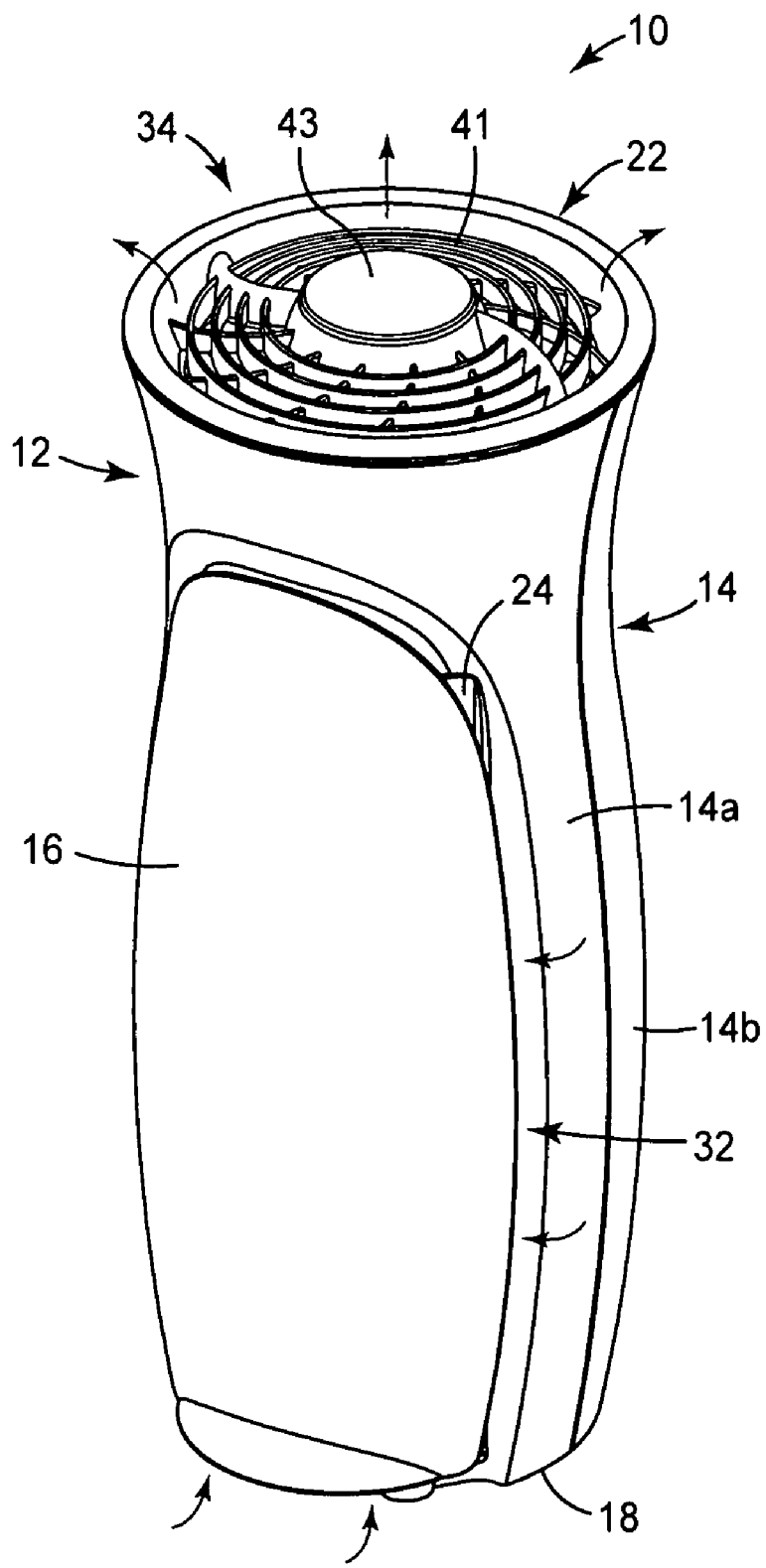
FIG. 1 is perspective view of an air purifier apparatus made according to the present description.

Reference is made to FIGS. 1-4 for illustrating one exemplary embodiment of the present description that is directed to a portable air purifier apparatus 10 and method for filtering and purifying air within a space, such as a room, which overcomes and minimizes the drawbacks and shortcomings noted above. While the present description is in the context of a portable air purifier apparatus 10 for use in an indoor space, it will be appreciated that the principles and scope of the present description envision its use in other purifying and filtering apparatus and systems. For example, the apparatus and method for filtering and purifying air may be used in furnaces, air conditioning units and the like.

Included in the air purifier apparatus 10 is a housing assembly 12 that is portable. Also, the air purifier apparatus 10 may be wall mounted. In the exemplary embodiment, the housing assembly 12 includes an upright main housing body 14 having a pair of mating housing portions 14a and 14b and a removable panel 16. The main housing body 14 has a bottom platform 18 for supporting the air purifier apparatus 10 in a standing condition. The main housing body 14 includes a generally tubular-shaped construction defining an upstanding cavity 20 (FIG. 3) for allowing passage of air therethrough as well as for accommodation of at least an air moving system 22, such as a fan system 22. The air moving or fan system 22 includes a cowling or housing 23, a filtering mechanism 24 and an ionizer system 26 made according to the principles of the present description. It will be appreciated that a wide variety of construction shapes and sizes may be provided for the housing assembly 12 and the present description is not limited by the configuration and relative sizes described and illustrated herein. The housing assembly 12 may be made of any suitable material(s) or combinations thereof and include, but is not limited to electrically insulating materials, such as thermoplastics as ABS, polybutylene terephthalate (PBT), polyethylene terephthalate (PET), polycarbonate (PC), polystyrene (PS), and the like.

The removable panel 16 has a generally elongated and at least partially circumferentially extending construction. The removable panel 16 may be sized and shaped to cover an elongated opening 28 in a wall portion 30 of the main housing body portion 14a. The removable panel 16 is removably attached to the main housing body 14 as by an attaching mechanism (not shown) or other similar type of securing mechanism located in the bottom of the removable panel 16 that mates with openings (not shown) formed in mounting structure 29 on the housing portion 14a. The attaching mechanism may be configured to releasably engage a portion of the main housing body for securely attaching the removable panel to the main housing body. As such, the removable panel 16 allows access to the interior cavity 20 of the housing assembly 12 so as to, for example, permit replacement of the filtering mechanism 24 at stated intervals. Also, the combination and arrangement of the removable panel 16, opening 28, and the main housing body 12 allow formation of an inlet openings 32 extending around the removable panel and into the cavity 20. In this embodiment, the inlet opening 32 is formed about a portion of the periphery of the removable panel 16. Another inlet opening (not shown) is formed adjacent a flared out bottom portion of the removable panel 16 to permit sufficient air intake for the air treatment intended. The present description contemplates other embodiments, wherein a plurality of inlet openings may be provided. For example, intake openings may be provided in the panel and/or the main housing body.

Figure 3:
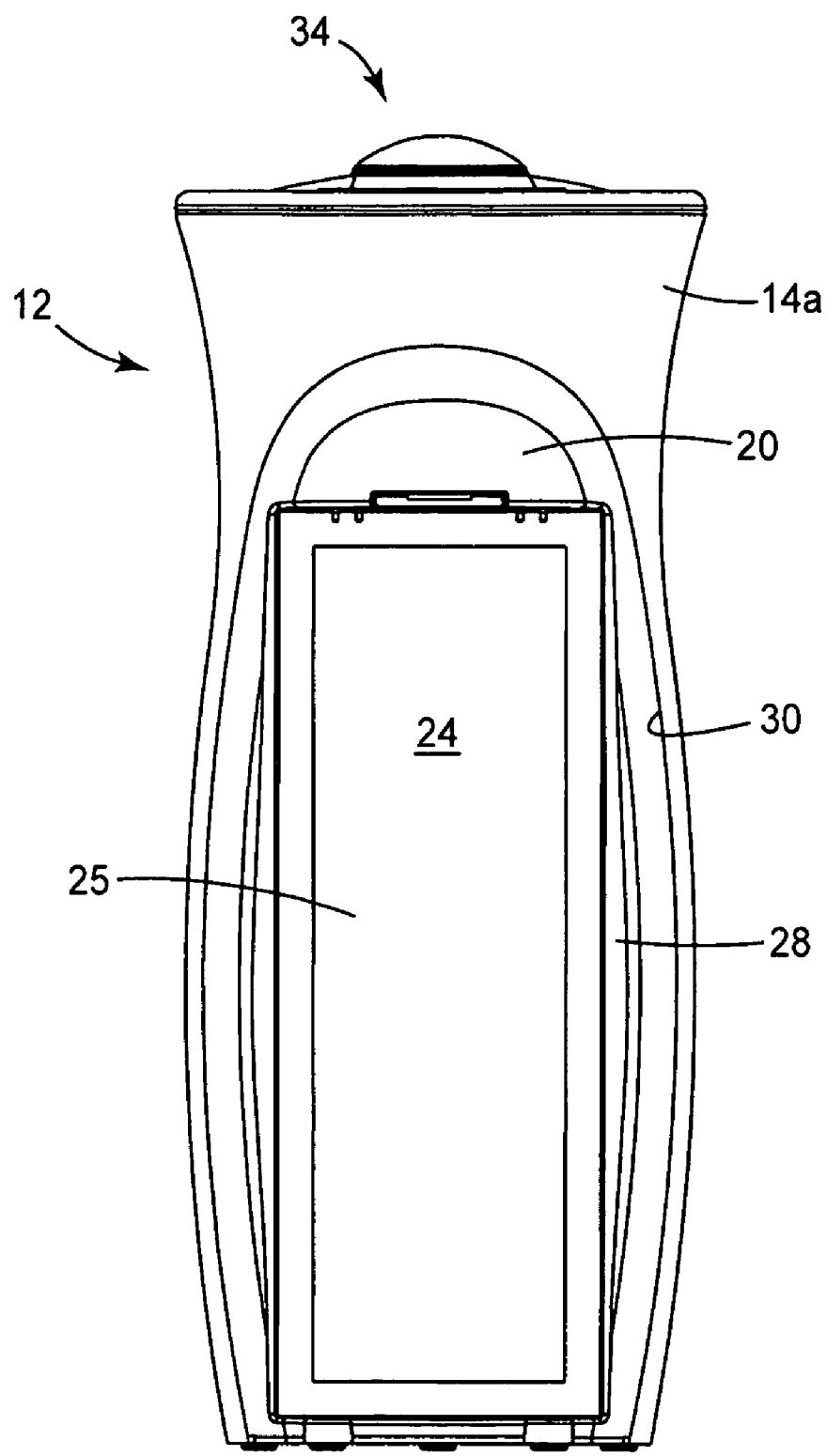
FIG. 3 is a view similar to FIG. 1, but with a front housing panel removed for illustrating some of the components of the air purifier of the present description.
Figure 4:
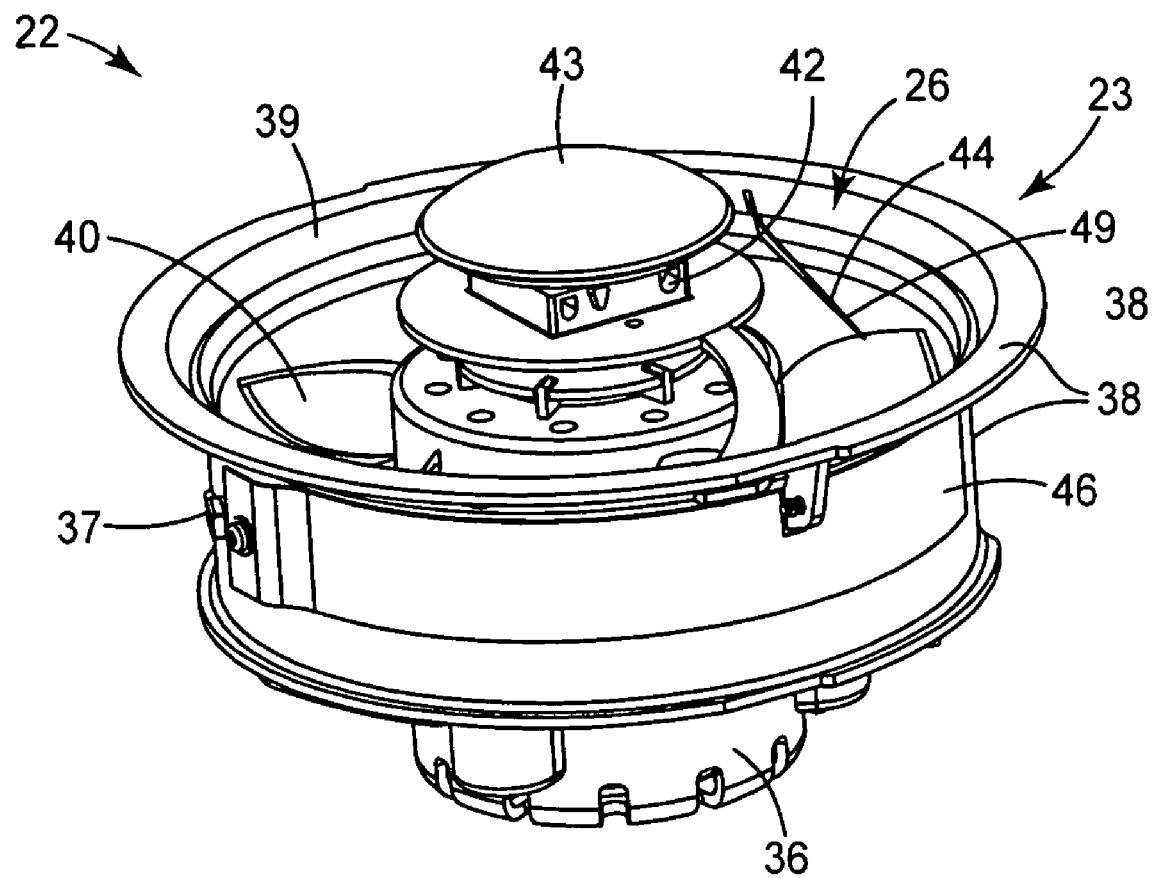
FIG. 4 is an enlarged and fragmented view fan system and ionizer system according to the present description.

Reference is made to FIGS. 3 & 4 for illustrating that the housing assembly 12 includes an exit opening 34 or outlet 34, downstream of the cavity 20, defined in an exposed upper end portion of the main housing body 14. The fan system 22 includes a fan motor 36 that is secured to the cowling 23 that is positioned immediately adjacent the outlet 34 and defines an air opening or passage 39 through the cowling. The fan system 22 is operable for rotatably driving a plurality of blades 40 extending radially from a rotor thereof within the air passage. The blades 40, when driven, draw air upstream of them, through the inlet opening 32, and discharges air, downstream of them through the outlet opening 34 including a grill 41 may be made of an insulating material. The fan motor 36 may be any suitable type used in portable air purifier systems and powered from any suitable source, such as an AC power source. The fan motor 36 is under the control of a control unit generally indicated by reference numeral 42 that includes a manually operated power switch. The fan motor and control unit may be similar to that used in the FAP04-RC Ultra-Slim Air Purifier for purifying room air that is commercially available from 3M Corporation, St. Paul, Minn. The control unit may control the turning 'on' and 'off' of power to operate the fan and the ionizer responsive to normal operation of the switch. The ionizer may be powered for ionizing while the fan motor is operated. It will be appreciated that only those portions of the fan motor and control unit that are needed to understand the present description are provided.

Figure 2:
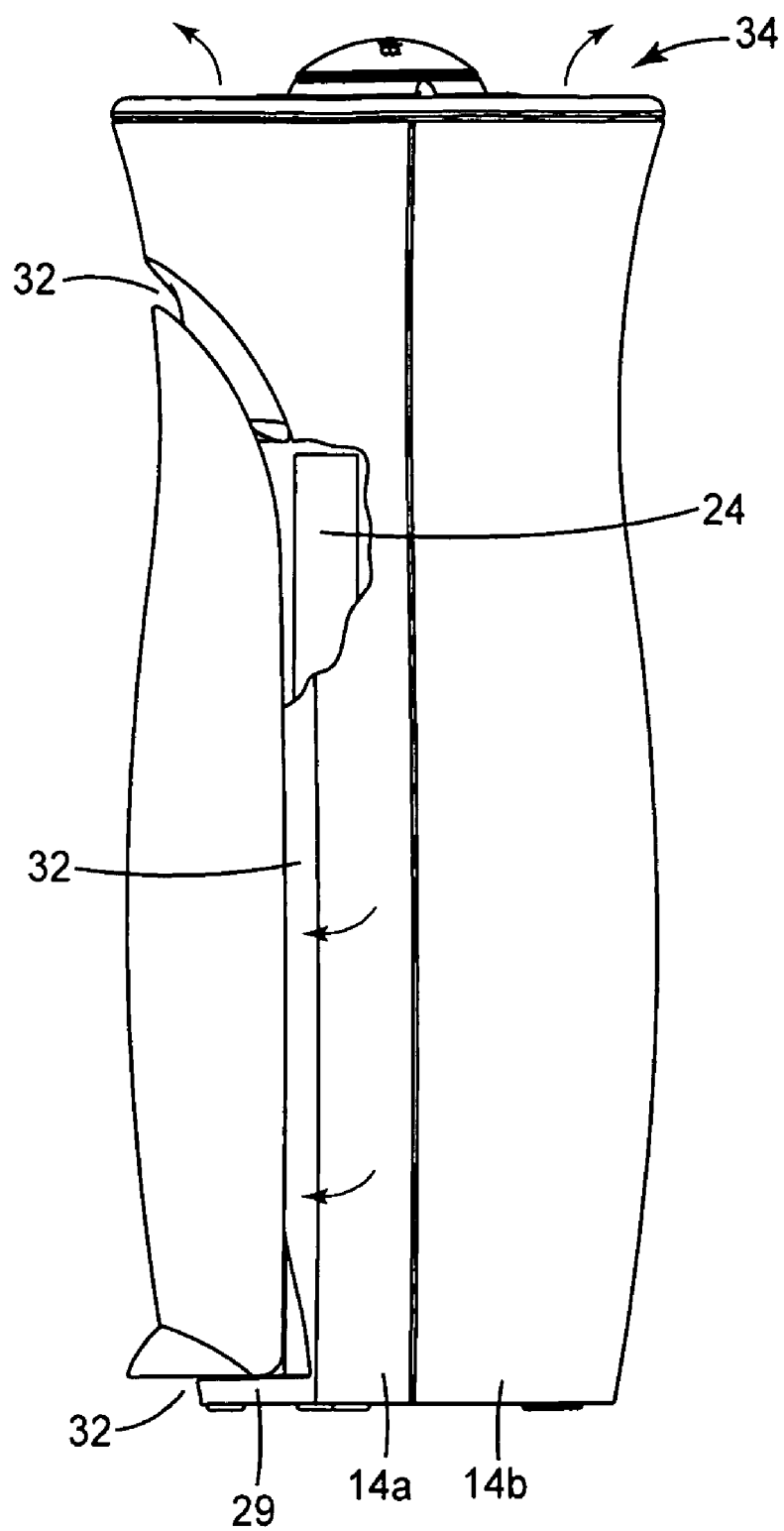
FIG. 2 is a side elevation view of the air purifier apparatus illustrated in FIG. 1.

Reference is now made to FIG. 2 for illustrating one exemplary embodiment of a known type of filtering mechanism 24 that is removably mounted on a mounting assembly in the housing assembly 12 as by any known and suitable approach. The filtering mechanism 24 may be of the type that is replaceable through the elongated opening 28. In the exemplary embodiment, it will be appreciated that the present description contemplates use of a wide variety of filters for the filtering mechanism 24. In the exemplary embodiment, the filtering mechanism 24 may include at least one filter media element 25 on a rectangular frame that performs both mechanical and electrostatic filtering. Such a filtering mechanism purifies and removes contaminants of various sizes, such as smoke particulate, from air flowing in the cavity 20. Such filter media provide collection surfaces that are permanently electret charged with respect to ground so that electrical charges of the ionized molecules will be attracted to the filter. The charged fibers of the filter media attract the floating charged dust particles.

The present description contemplates that non-woven polymeric fibrous webs can be improved by transforming the web into an electret, i.e., a dielectric material exhibiting a quasi-permanent electrical charge. Electrets are effective in enhancing particle capture in aerosol filters. Electrets are useful in a variety of devices including, e.g., air filters. Melt-blown, electrically charged fibers can be formed from materials that have acquired a charge be it positive only, negative only, or both positive and negative. Electrets may be made from synthetic polymers e.g., fluoropolymers, polypropylene, and polyethylene terephthalate. While the foregoing materials are exemplary, others may be used. Representative examples of commercially available electrically charged fibers suitable include "FILTRETE" fibers, commercially available from 3M Corporation, St. Paul, Minn. "FILTRETE" fibers are electret fibers, i.e., fibers in which a permanent state of charge has been set up. The filter media may also be of the type used in the previously noted FAP04-RC Ultra-Slim Air Purifier for rooms as noted above. As such, the air purifier system may offer a cleaning rate similar to a HEPA air purifier for a comparable room size as defined by the room size definition and calculation procedure of the AHAM Room Air Cleaner Certification Program.

Although not shown, the filtering mechanism 24 may be provided with a filter monitor (not shown), such as a timer, for indicating when a filter is in need of replacement. It will be appreciated that the larger the filter resistance the more powerful the fan must be to draw the air through.

As noted, known generated electrostatic voltage fields in air purifiers tend to be transient in terms of time inasmuch as such fields tend to collapse due to the build-up or accumulation of static charges. In particular, accumulation tends to lower the voltage potential between the electrode and the surrounding environment. Accordingly, the ion current and, thus ionization of the air molecules is effectively reduced, thereby effectively reducing the efficiency of the air purification and filtration apparatus. The present description is directed to generally maintaining the consistency of a voltage field relative to an air outlet of an air purifier or the like over a predefined period of time so as to increase efficiency of the particulate removal process since a sufficient amount of ions may interact with the passing air. The present description is directed to generally maintaining the consistency of a voltage field relative to an air outlet of an air purifier or the like over a predefined period of time. This increases the efficiency of the particulate removal process since a sufficient amount of ions may interact with the passing air.

The voltage field is generated from at least the point high voltage source 44 in the outlet 34. The noted controlling of the accumulation or build-up of electrons deposited on an insulating housing structure 38 surrounding the opening or passage 39 occurs by bleeding such accumulation to a significantly lower potential or ground potential surface. Ideally, the controlling of the charge accumulation or build-up by a bleeding electrode 46 occurs downstream of the point source. But, in some cases the controlling may occur slightly upstream of the point source. The relative positioning of the point source and the controlling bleeding electrode may be determined by the ease of maintaining the voltage field generally consistent over a predefined period of time that would correspond to maintain the CADR in a desired range. According to the present description such consistency of the voltage field is generally prolonged relative to known air purifier systems.

In the exemplary embodiment, the point source 44 may be defined by at least one high voltage electrode 44 under control of the control unit. A distal end 49 of the electrode 44 protrudes from the fan housing portion 38 slightly downstream of the blades and its operation for ionizing is under the control of the control unit as noted above. The control unit may be operated so as to cause the electrons to flow into and from the distal end 49 as is known. The electrode 44 creates a flow of electrons to interact with the gaseous medium and create an effective voltage field across the opening. For purposes of illustration, the high voltage may be in the order of about +/−4-20 kV when measured with a high voltage meter having a 1 G$\Omega$ input impedance and about +/−4-30 kV when measured with a high voltage meter having 10 G$\Omega$ input impedance. These values are for illustration purposes and should not be considered limiting. In the illustrated exemplary embodiment, the electrode 44 having the shape of a thin and flat needle shaped element. The needle element may have a relatively sharp point at its distal end 49 at which discharge of the electrons occurs. Other electrode shapes and sizes are envisioned. For example, these voltage discharge electrodes or elements may also include a wire(s), or other conductive elements that come to some kind of a point. While a single electrode is illustrated, it will be appreciated that a plurality of electrodes may be used, such as brushes or a plurality of single electrodes or wires. Whatever configuration is used, the electrode or the electrode configurations and positions should provide a sufficient voltage field in the outlet to ionize the air as intended. Also, while electrons are flowing from the electrode, the present description envisions that electrons may flow into the needle element.

In the illustrated exemplary embodiment, the build-up or accumulation is discharged by a bleeding electrode 46 through the insulating material. Accordingly, the attraction developed by the bleeding electrode 46 and the conductivity of the insulating structure 38 of the purifier surrounding the opening 39 control migration of the electrons from the point source to the bleeding electrode. Accordingly, any excessive accumulation that might be detrimental to maintaining an effective voltage field will be discharged and controlled. Stated differently, the bleeding electrode as it is constructed and arranged controls the accumulation of charges on structure surrounding the opening that affect the voltage field by bleeding the charges therefrom in a manner that generally maintains the effective voltage field across the opening. In the illustrated exemplary embodiment, the bleeding electrode 46 may be a strip of conductive tape 46 that has a significant predetermined surface area in order to discharge the excessive charges. The conductive tape 46 may be metal or some other conductive material. It will be appreciated that other types of conductive elements may be provided which are made of a conductive strip and the like. A conductive coating may be applied to the insulating housing material. Grounding may occur as a result of conductive points or small areas. Furthermore, the housing cowling assembly 38 may be multi-layered with one layer being made of an insulating material and an alternate layer made of a conductive material. It will be further understood that grounding or discharge of the charges by the bleeding electrode need not be to earth ground, but at a significantly lower voltage than the high voltage point source. In the present description, the fan motor may also be electrically coupled to the conductive strip or electrode 46 by lead 37. Also, grounding may be obtained by an insulated wire or the like that extends into or is immediately adjacent the voltage field.

Moreover, the conductivity of the insulating cowling housing assembly 38 may be such to control migration of the electrons that accumulate from the electrode. The housing assembly 38 may be made of a plastic insulating material having conductivity that controls such migration. Clearly, the conductivity should not be such as to make it a perfect insulating material, since that would prevent migration and thereby discharge of the accumulation or build-up. Conversely, the insulating material should not be so conductive that it serves to break down the desired voltage field or excessively bleed charge. The present description envisions that the insulating material may include, but not be limited to thermoplastics as ABS, polybutylene terephthalate (PBT), polyethylene terephthalate (PET), polycarbonate (PC), polystyrene (PS), and the like.

This present description may take on various modifications and alterations without departing from the spirit and scope. Accordingly, this present description is not limited to the above-described exemplary embodiments, but is to be controlled by limitations set forth in the following claims and any equivalents thereof. This present description also may be suitably practiced in the absence of any element not specifically disclosed herein. All patents and publications noted above, including any in the Background section are incorporated by reference into this document in total.

What is claimed is:

1. A system comprising:
    a housing assembly defining an opening allowing air to pass therethrough; a motor driven fan associated with the housing assembly and operable for driving the air through the opening downstream of the opening;
    at least a high voltage source within the opening and/or adjacent the opening to ionize and transfer charges to molecules in the air, and create an effective voltage field across the opening;
    at least one charge bleeding element adjacent the opening and associated with the housing assembly with the bleeding element at a lower voltage potential than the high voltage source; and
    an insulating material between the bleeding element and the high voltage source for controlling migration of charges to the bleeding element that accumulate on the housing assembly so as to generally maintain an effective voltage field over a period of time across the opening.

2. The system of claim 1, further comprising: a filter mechanism that includes charged fibers.

3. The system of claim 1, further including a plurality of high voltage point sources.

4. The system of claim 3, wherein the plurality of high voltage point sources include at least one of a group of high voltage point sources consisting of: electrodes, needles, wires, brushes, and combinations thereof.

5. The system of claim 1, wherein the high voltage source includes at least one of a group of high voltage point sources consisting of electrodes, needles, wires, brushes, and combinations thereof.

6. The system of claim 1, wherein the insulating material includes at least one of a group consisting of: thermoplastics, ABS, polybutylene terephthalate (PBT), polyethylene terephthalate (PET), polycarbonate (PC), polystyrene (PS), and combinations thereof.

7. The system of claim 1, wherein the bleeding element has a predefined area which controls migration of the charges thereto.

8. The system of claim 1, wherein the bleeding element is ground.

9. The system of claim 1, further including a motor driven fan associated with the housing assembly and operable for driving a gaseous medium through the opening downstream of the opening, wherein the motor is grounded to the charge bleeding element.

10. An air purifier apparatus for removing contaminants from air, the apparatus comprising:
    a housing assembly defining an opening allowing air to pass therethrough
    a motor driven fan associated with the housing assembly and operable for driving the air through the opening downstream of the opening;
    at least a high voltage source within the opening and/or adjacent the opening to ionize the air, and create an effective voltage field across the opening;
    at least one charge bleeding element adjacent the opening and associated with the housing assembly with the bleeding element at a lower voltage potential than the high voltage source, and the bleeding element is shielded by an insulating material for controlling migration of charges that accumulate on the housing assembly to the bleeding element so as to generally maintain an effective voltage field across the opening; and
    a filter mechanism in the housing assembly that is located upstream of the opening for removing contaminants from the air.

* * * * *